United States Patent [19]
Tanner et al.

[11] Patent Number: 6,162,961
[45] Date of Patent: Dec. 19, 2000

[54] ABSORBENT ARTICLE

[75] Inventors: James Jay Tanner, Winneconne; Victor Michael Gentile, Appleton, both of Wis.

[73] Assignee: Kimberly-Clark Worldwide, Inc., Neenah, Wis.

[21] Appl. No.: 09/290,092

[22] Filed: Apr. 12, 1999

Related U.S. Application Data

[60] Provisional application No. 60/081,968, Apr. 16, 1998.

[51] Int. Cl.$^7$ .................................................. A61F 13/15
[52] U.S. Cl. ............................................ 604/374; 604/367
[58] Field of Search ............................. 604/385.01, 367, 604/374, 375; 162/100, 109; 428/171

[56] References Cited

U.S. PATENT DOCUMENTS

| | | | |
|---|---|---|---|
| 3,512,530 | 5/1970 | Jones, Sr. ............................... | 128/290 |
| 3,736,931 | 6/1973 | Glassman ............................ | 128/290 R |
| 3,844,288 | 10/1974 | Kiela ...................................... | 128/287 |
| 4,057,061 | 11/1977 | Ishikawa et al. ..................... | 128/284 |
| 4,100,324 | 7/1978 | Anderson et al. ..................... | 428/288 |
| 4,215,212 | 7/1980 | Franks ................................... | 536/57 |
| 4,275,811 | 6/1981 | Miller .................................... | 206/204 |
| 4,321,997 | 3/1982 | Miller .................................... | 206/204 |
| 4,382,507 | 5/1983 | Miller .................................... | 206/204 |
| 4,410,578 | 10/1983 | Miller .................................... | 428/117 |
| 4,537,655 | 8/1985 | Henriksson et al. ..................... | 162/23 |
| 4,544,596 | 10/1985 | Holtman ................................ | 428/171 |
| 4,560,527 | 12/1985 | Harke et al. ........................... | 264/500 |
| 4,619,862 | 10/1986 | Sokolowski et al. ................... | 428/221 |
| 4,621,011 | 11/1986 | Fleischer et al. ....................... | 428/221 |
| 4,689,118 | 8/1987 | Makoui et al. ......................... | 162/100 |
| 4,735,846 | 4/1988 | Larsonneur ............................ | 428/198 |
| 4,767,848 | 8/1988 | Makoui et al. ......................... | 536/56 |
| 4,770,920 | 9/1988 | Larsonneur ............................ | 428/198 |
| 4,822,452 | 4/1989 | Tse et al. ................................ | 162/146 |
| 4,879,170 | 11/1989 | Radwanski et al. .................... | 428/233 |
| 4,931,355 | 6/1990 | Radwanski et al. .................... | 428/283 |
| 4,940,621 | 7/1990 | Rhodes et al. ......................... | 428/137 |
| 4,950,262 | 8/1990 | Takagi .................................... | 604/385.1 |
| 5,022,945 | 6/1991 | Rhodes et al. ......................... | 156/253 |
| 5,055,332 | 10/1991 | Rhodes et al. ......................... | 428/74 |
| 5,137,537 | 8/1992 | Herron et al. .......................... | 8/120 |
| 5,183,707 | 2/1993 | Herron et al. .......................... | 428/364 |
| 5,242,435 | 9/1993 | Murji et al. ............................ | 604/374 |
| 5,295,986 | 3/1994 | Zehner et al. .......................... | 604/385.1 |
| 5,308,896 | 5/1994 | Hansen et al. ......................... | 524/13 |

(List continued on next page.)

FOREIGN PATENT DOCUMENTS

| | | |
|---|---|---|
| 0 293 208 B1 | 7/1991 | European Pat. Off. . |
| 0 804 912 A1 | 11/1997 | European Pat. Off. . |
| 0 804 913 A1 | 11/1997 | European Pat. Off. . |
| 0 804 916 A1 | 11/1997 | European Pat. Off. . |
| 0 804 917 A1 | 11/1997 | European Pat. Off. . |
| WO 96/38232 A1 | 12/1996 | WIPO . |

OTHER PUBLICATIONS

Derwent World Patent Database abstract of JP 92–08787 A: Description of Daiwa Kagaku Kogyo KK; Sanyo Chem Ind. Ltd., "Antimicrobial Water–Absorbing Resin Composition For Packaging."

"Absorbent Core Technology for Personal Care Products," *Teltech Research Services Monthly Update*, Mar. 1999, pp. 1–8.

*Primary Examiner*—Dennis Ruhl
*Attorney, Agent, or Firm*—Thomas J. Connelly

[57] ABSTRACT

An absorbent article having exceptional expansion properties when wetted by an aqueous fluid is disclosed. The absorbent article has an absorbent member formed from a multitude of randomly oriented cellulosic fibers containing at least about 20% lignin. The absorbent member has a moisture content of from between about 1% to about 20% water by weight of fiber and the fibers are elastically stressed and bonded by hydrogen bonds. The fibers are retained in a stressed condition and have a density of from between about 0.2 g/cc to about 1 g/cc.

21 Claims, 6 Drawing Sheets

U.S. PATENT DOCUMENTS

| | | | |
|---|---|---|---|
| 5,320,895 | 6/1994 | Larsonneur et al. | 428/137 |
| 5,374,260 | 12/1994 | Lemay et al. | 604/378 |
| 5,387,385 | 2/1995 | Murji et al. | 264/160 |
| 5,399,412 | 3/1995 | Sudall et al. | 428/153 |
| 5,409,572 | 4/1995 | Kershaw et al. | 162/109 |
| 5,415,644 | 5/1995 | Enloe | 604/385.2 |
| 5,466,232 | 11/1995 | Cadieux et al. | 604/378 |
| 5,484,896 | 1/1996 | Naieni et al. | 530/504 |
| 5,492,753 | 2/1996 | Levy et al. | 428/219 |
| 5,547,745 | 8/1996 | Hansen et al. | 428/283 |
| 5,549,791 | 8/1996 | Herron et al. | 162/157.6 |
| 5,582,606 | 12/1996 | Bruemmer et al. | 604/385.2 |
| 5,620,431 | 4/1997 | LeMahieu et al. | 604/385.2 |
| 5,634,915 | 6/1997 | Osterdahl | 604/379 |
| 5,649,918 | 7/1997 | Schleinz | 604/385.2 |
| 5,672,248 | 9/1997 | Wendt et al. | 162/109 |
| 5,703,225 | 12/1997 | Shet et al. | 536/59 |
| 5,728,085 | 3/1998 | Widlund et al. | 604/378 |
| 5,730,737 | 3/1998 | Widlund et al. | 604/378 |
| 5,779,860 | 7/1998 | Hollenberg et al. | 162/206 |
| 5,814,034 | 9/1998 | Widlund et al. | 604/367 |
| 5,817,085 | 10/1998 | Widlund et al. | 604/379 |

ABSORBENT ARTICLE

This application claims benefit of Provisional Application No. 60/081,968, filed Apr. 16, 1998.

FIELD OF THE INVENTION

This invention relates to an absorbent article having exceptional expansion properties when wetted by an aqueous fluid. More specifically, this invention relates to an absorbent article constructed from an absorbent having unique expansion properties.

BACKGROUND OF THE INVENTION

Most traditional absorbent structures consist of a static network of fibers that contain a plurality of open areas located between the fibers. The open areas retain aqueous fluid that is absorbed by the absorbent structure. The majority of fluid is not absorbed into each individual fiber but instead most fluid is retained within the empty spaces that are formed in the network of cellulosic fibers. If the traditional absorbent member has a high absorbent capacity it usually does not have a high wicking rate. The reason for this is that the first attribute is in conflict with the second attribute.

Efforts to find absorbent members which have both a high absorbent capacity as well as a high wicking rate have only been marginally successful. It has been recognized that the dynamic properties of the fibers themselves somehow have to be changed. Some success has been obtained in calendering a wet laid network of bleached chemi-thermo-mechanical pulp (BCTMP). For this material, small expansion or release of potential energy upon wetting of the absorbent fibers was observed which could enhance the absorbent capacity and wicking rate of the absorbent member. It is believed that this occurs because the absorbent fibers are oriented, to a large extent, in the horizontal plane but with some modest "z" direction to the fiber axis as they conform to an irregular surface of the forming wire.

Today, there are a number of applications for absorbent products, both disposable and reusable, which can take advantage of the expansion properties of the absorbent. For example, an absorbent having a rapid expansion capability primarily in one direction can be used in an infant diaper to form a gasket with the legs of the infants as the absorbent expands. This decreases the chance of leakage through the leg cuffs. A second example is the use of an absorbent pad in conjunction with a retail package containing perishable food, i.e. meats and poultry. As the food item gives up juices, blood, water, and other liquids, the absorbent pad can quickly expand to absorb this fluid so that an appealing retail package of food can be presented to the consumer. Still another example is the absorbent material that is placed between the joint of two abutting pipe flanges to provide a water tight seal. The use of an absorbent with tremendous expansion capabilities is advantageous in this situation for it assure that as the absorbent swells, the gasket or seal will become tighter and prevent leakage.

Now it has been recognized that there is a real need for an absorbent member to be used in an absorbent article which has a high absorbent capacity, a high wicking rate and the ability to rapidly expand in at least one direction when wetted by an aqueous fluid.

SUMMARY OF THE INVENTION

Briefly, this invention relates to an absorbent article having exceptional expansion properties when wetted by an aqueous fluid. The absorbent article has an absorbent member formed from a multitude of randomly oriented cellulosic fibers containing at least about 20 percent lignin. The absorbent member has a moisture content of from between about 1 percent to about 20 percent water by weight of fiber and the fibers are elastically stressed and bonded by hydrogen bonds. The fibers are retained in a stressed condition and have a density of from between about 0.2 g/cc to about 1 g/cc.

The general object of this invention is to provide an absorbent article having exceptional expansion properties when wetted by an aqueous fluid. A more specific object of this invention is to provide an absorbent that has unique expansion properties and can be used in a variety of disposable products.

Another object of this invention is to provide an absorbent article that is economical to produce.

A further object of this invention is to provide an inexpensive absorbent article that can be used for many different applications.

Still another object of this invention is to provide an absorbent article that can expand up to about 8 times its original volume.

Still further, an object of this invention is to provide an absorbent article that is easy to manufacture and can be formed into a variety of different shapes and configurations.

Other objects and advantages of the present invention will become more apparent to those skilled in the art in view of the following description and the accompanying drawings.

DETAILED DESCRIPTION OF THE PREFERRED EMBODIMENTS

Figure 1:
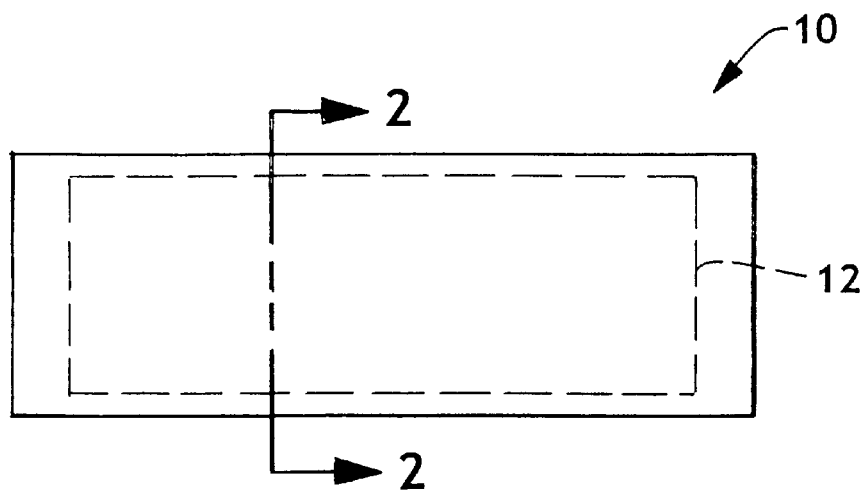
FIG. 1 is a top view of an absorbent article having exceptional expansion properties when wetted by an aqueous fluid.
Figure 2:
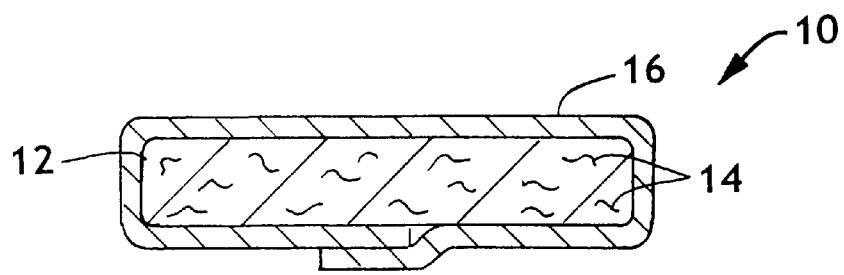
FIG. 2 is a cross-sectional view of the absorbent article shown in FIG. 1 taken along line 2—2.

Referring to FIGS. 1 and 2, an absorbent article 10 is shown which includes an absorbent member 12 constructed from a multitude of randomly oriented cellulosic fibers 14. The absorbent article 10 has high absorbent capacity and exhibits exceptional expansion properties when wetted by an aqueous fluid, such as water. The fibers 14 have an average length of from between about 1 millimeter (mm) to about 5 mm and are preferably cellulosic softwood fibers that are relatively stiff. The fibers 14 are randomly oriented and elastically stressed or strained in one or more selected directions. Preferably, the fibers 14 are chemi-thermo-mechanical softwood fibers, and most preferably, they are bleached chemi-thermo-mechanical softwood fiber. The bleaching masks the yellow color that occurs because of the high percentage of lignin that is retained within each fiber.

Preferably, the fibers 14 should be non-linear in configuration. At least a majority of the fibers 14 should be non-linear in configuration and exhibit a curved, bent, crimped, kinked, arcuate, contorted, curled or some other non-linear shape. By "kinked" it is meant a tight bend or a sharp twist in a tube-like fiber. It should be noted that the entire fiber 14 does not have to be curved, bent, crimped, kinked, etc. but that at least a portion of the fiber 14 should exhibit a non-linear geometrical shape. The more each fiber 14 is contorted or formed into a non-linear shape, the better the absorbent properties of the absorbent 12. Linear fibers can be used but they should only represent a minority of the overall fibers present. Preferably, less than about 40 percent of the fibers 14 should be linear.

Each fiber 14 should contain at least about 20% lignin and with the remaining 80% being cellulosic materials, which includes cellulose plus hemicellulose and other minor wood components. Lignin is the chief non-carbohydrate constituent of wood and other fibrous plants. Lignin is a polymer that functions as a natural binder and provides support for the cellulosic fibers. The lignin is present both within each fiber and between adjacent fibers. For purposes of this invention, it is important that the required percent of lignin be present within each fiber 14. The presence of the lignin within each fiber 14 makes the fibers 14 stiffer and more difficult to bend. This is a major difference from traditional unbonded cellulosic absorbent fibers which are typically bleached southern softwood Kraft fibers which contain very little, if any, lignin within the fiber itself. Hence, the traditional fibers are soft and limp. Lignin functions as a thermoplastic reinforcing material that allows the fibers to return to a natural tubular state upon wetting. Cellulose and hemicellulose give the fibers hydrophilic properties and the ability to form hydrogen bonds in the presence of small amounts of water.

The fibers 14 that form the absorbent member 12 should be randomly oriented and densely compacted. The primary axis of each of the fibers 14 can be oriented in the x-direction, in the y-direction or in the z-direction. This three dimensional, random orientation is beneficial in creating a high absorbent capacity and a high wicking rate within the absorbent member 12. To the contrary, most traditional fibers that have been wet-laid into a fibrous sheet have virtually all of the fibers laid with their long axis in the x-y plane and a significant number of the fibers 14 lie in the machine direction (MD) or x-direction. Essentially none of the wet-laid fibers are oriented in the vertical or z-direction.

The fibers 14 of this invention are stressed into an extremely compacted condition to form an entangled mass which is held together by a plurality of hydrogen bonds. Some of the fibers 14 are held in compression, some in bending and some in shear. The hydrogen bonds can be both inter fiber hydrogen bonds and intra fiber hydrogen bonds. This is an environment wherein almost every fiber 14 is retained in a stressed or non-relaxed condition. The stress forces may be applied in more than one direction.

Figure 3:
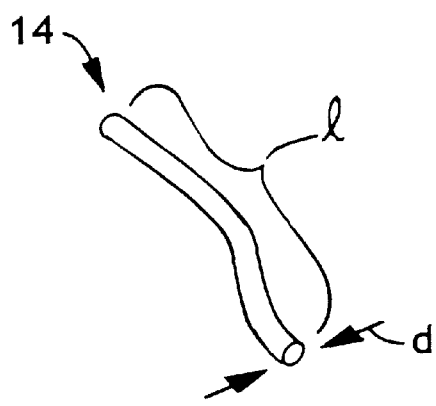
FIG. 3 is a perspective view of an individual cellulosic fiber.

Referring now to FIG. 3, an individual fiber 14 is shown having a diameter "d" of less than about 50 microns. Preferably, the diameter "d" ranges from between about 10 microns to about 40 microns, and most preferably, the diameter "d" ranges from between about 20 microns to about 30 microns. Each fiber 14 also has a length "l" of less than about 5 millimeters (mm), preferably the length "l" is from between about 1 mm to about 5 mm, and most preferably, the length "l" is from between about 1 mm to about 3 mm. As with most natural materials, there is a distribution of properties, so that stated dimensions do not limit this invention.

Each cellulosic fiber 14 has a moisture content of from between about 1% to about 20% water by weight of fiber. Preferably, the moisture content of each fiber 14 is from between about 2 to about 15% water by weight of fiber. Most preferably, the moisture content of each fiber 14 is from between about 5 to about 15% water by weight of fiber. This level of moisture is required to obtain hydrogen bonding. However, the absorbent 12 could be heated until dry after bonding where the moisture level within the absorbent 12 has essentially dropped to zero. The cellulosic fibers 14 in a non-stressed, unbonded condition have a bulk density of at least 0.01 grams per cubic centimeter (g/cc). Preferably, the bulk density of all the non-stressed fibers 14 is from between about 0.02 g/cc to about 0.1 g/cc, and most preferably, the bulk density of all the non-stressed fibers 14 is from between about 0.05 g/cc to about 0.08 g/cc. The low bulk density of the cluster of non-stressed, unbonded fibers allows for a high level a stress to be induced into the fibers just before bonding them together.

Referring again to FIGS. 1 and 2, it should be noted that the absorbent member 12, when the cellulosic fibers 14 are in an elastically stressed condition, will have a density, sometimes referred to as "bulk density," of from between about 0.2 g/cc to about 1 g/cc. Preferably, the bulk density of the absorbent 12 is between about 0.2 g/cc to about 0.8 g/cc, and most preferably, the bulk density of the absorbent 12 is between about 0.5 g/cc to about 0.8 g/cc. This density is still below the density of the cellulose walls of the individual fibers 14, which is approximately 1.4 g/cc. Therefore, there is still a significant but reduced amount of open space in the stressed and bonded absorbent member 12, about 33 percent versus 98.6 percent for an unstressed and unbonded air laid absorbent structure of fibers.

Figure 4:
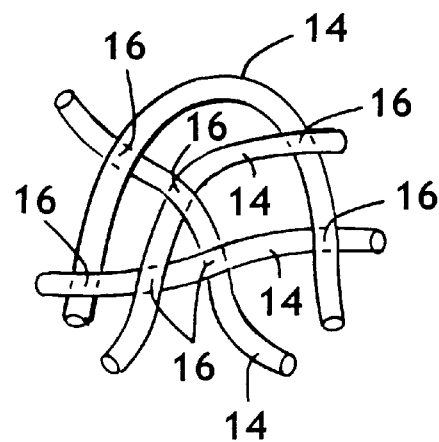
FIG. 4 is a perspective view of four randomly oriented fibers that are bonded together by hydrogen bonds.

Referring now to FIG. 4, four randomly oriented fibers 14 are shown bonded together by a multitude of hydrogen bonds 16. A hydrogen bond is a weak chemical bond formed between an electronegative oxygen atom and a hydrogen atom already bonded to another electronegative oxygen atom. The hydrogen bonds 16 cause the fibers surfaces 14 to be attached to adjacent fiber surfaces. Hydrogen bonding will occur within fibers as well. This condition can occur when, for example, a tubular fiber is twisted or bent and the circular open lumen cross-section collapses to a flattened elliptical shape. When two or more different points inside the lumen touch or are forced together under pressure or stress, hydrogen bonding can occur. In the elastically stressed and bonded condition, the fibers 14 exhibit stored bending, compression and shear energy. Hydrogen bonds 16 form as the fiber surfaces 14 are brought into intimate contact under pressure. Water that is in or on the individual fibers 14 contribute to the intimate contact and formation of the bond even though there is still more liquid capacity in and around the fibers 14 (not saturated). As water leaves the contact point between the fibers 14 due to drying or migration to drier areas, surface tension makes two adjacent fibers or two areas or points inside a fiber lumen come closer together allowing hydrogen bonding to occur. The moisture of the absorbent member 12 should be less than about 15% water per unit weight of fiber. Preferably, the moisture of the absorbent member 12 should be from between about 5 to about 10% water per unit weight of fiber to allow enough hydrogen bonds to form to lock in the stressed high density condition. Insufficient moisture would inhibit hydrogen bond formation according to the mechanism described, while excessive moisture would disrupt the hydrogen bonds upon release of the stressing forces.

The hydrogen bonds 16 are relatively weak bonds but they are plentiful and sufficiently strong to lock in the stresses created in and between the fibers 14 as the fibers 14 are stressed into an extremely compacted form of the absorbent member 12. One method of constructing the absorbent member 12 is to collect randomly oriented fibers 14 in a hopper or vessel and then compress the fibers 14 from a single direction into a sheet of fibers. Experimental testing has indicated that when the cellulosic fibers 14 are compressed in only one direction, for example, in the z-direction, then the greatest expansion will occur opposite to this direction of compression.

Experimental testing has also revealed that the fibers 14 can be compressed from two or more directions, either simultaneously or sequentially. When the absorbent member 12 is compressed in two or more directions and later wetted by an aqueous fluid, rapid expansion in directions opposite to the directions of compression will occur. This feature is important for it will allow a manufacturer to construct an absorbent member 12 which can be tailored to the environment in which it is designed to function. For example, if it is desirable to construct a diaper with an absorbent member 12 which will rapidly expand in the y and z directions, then the absorbent member 12 can be compressed during formation in two directions opposite to these two directions. During use in the diaper, the absorbent member 12 will experience very little expansion in the x-direction but will exhibit substantial and rapid expansion in both the y and z-directions (the z-direction is the radial direction). The usefulness of being able to construct an absorbent member 12 with such expansion properties will be readily apparent to those skilled in the art of disposable absorbent products.

It has been mentioned earlier that the expansion occurs as an aqueous fluid wets the absorbent member 12. Aqueous fluids are defined for purposes of this invention as fluids that contain water or are similar to water. Representative fluids include tap water, distilled water, bottled water, urine, menses, human body fluids, emulsions of water plus hydrocarbons, etc. It should also be noted that non-aqueous fluids such as oils, non-polar hydrocarbons, etc. would not trigger the release of hydrogen bonds formed in and between the fibers.

As the absorbent member 12 is wetted, the hydrogen bonds 16 break and the stresses locked up in the individual fibers 14 of the absorbent member 12 are released. This causes the fibers 14 to move toward their original relaxed condition, which is a tubular shape, typically in a direction opposite to the direction from which they were stressed or compressed. As more and more hydrogen bonds 16 are broken, more and more fibers 14 are free to flex back to a less stressed or to a relaxed condition. As this occurs, open or void volume develops between the fibers 14. These voids are capable of receiving and containing the fluid that has insulted the absorbent member 12. The absorbent capacity of the absorbent member 12 is therefore increased and the absorbent member 12 becomes capable of receiving and holding greater quantities of fluid. The increased volume of the capillaries between fibers promotes a higher degree of fluid flow and wicking due to reduce friction or fluid drag. Thus, the absorbent member 12 performs differently from any known cellulosic product commercially sold today. Compressed regenerated cellulose sponges perform somewhat similarly but they are much more expensive to produce and cannot exert the pressure level of this invention.

The absorbent member 12 of this invention is unique in that the wet expansion rate is very rapid. The "wet expansion rate" is defined for purposes of this invention as the time it takes for the absorbent member 12 to expand to its maximum, (change in volume/unit time) once it is surrounded by an aqueous fluid, such as water. The "wet expansion rate" for some portion of the full expansion time can be determined by measuring the slope of the curve established by plotting the change in volume of the absorbent member 12 for each moment in time over the duration of the expansion. The "wet expansion rate" is related to the bulk density of the absorbent member 12 and to the depth of penetration that the fluid must travel to reach the midpoint or mid plane of the absorbent member 12. For example, a spherical shape, at a high density, denoted by the Greek letter rho "$\rho$", will have a slow maximum expansion rate for it has a low surface area to volume ratio (r) calculated by the formula $r=6/d$, where d is the diameter of the sphere. This can be contrasted to a thin sheet, like a piece of paper, where a high surface area to volume ratio (r) is found which can be calculated by the formula $r=2/t$, where t is equal to the thickness of the sheet. The expansion rate for the thin sheet will be faster than for the sphere assuming both have equal weights and equal densities. For a sphere and a sheet of paper of equal weight and density, their size relationship can be expressed by the formula $d=6 \text{ gsm}/\rho$. In this formula, "d" is the diameter of the sphere, "gsm" is the basis weight of the thin sheet in grams per square meter, and "$\rho$" is the density of both shapes.

The absorbent member 12 has the capacity to absorb from between about 1 to about 20 grams of aqueous fluid per gram of absorbent material. Preferably, the absorbent member 12 has the capacity to absorb from between about 1 to about 18 grams of aqueous fluid per gram of absorbent material. More preferably, the absorbent member 12 has the capacity to absorb from between about 1 to about 15 grams of aqueous fluid per gram of absorbent material. The absorbent member 12 is also capable of exhibiting rapid expansion. Starting with an absorbent member 12 having a predetermined initial volume, the absorbent member 12 is capable of expanding from between about 1 to about 8 times its initial volume as the absorbent member 12 absorbs an aqueous fluid. Preferably, the absorbent member 12 is capable of expanding from between about 5 to about 8 times its initial volume as the absorbent member 12 absorbs an aqueous fluid.

Returning to FIGS. 1 and 2, the absorbent article 10 also includes a cover 17 which is wrapped around the absorbent member 12 so as to at least partially, and preferably, completely enclose the absorbent member 12. The cover 17 can be liquid permeable or liquid-impermeable. If liquid-impermeable, a number of openings or apertures can be formed therein so as to allow fluid to reach the absorbent member 12. In the case where the absorbent article 10 is a disposable absorbent article, such as a bed pad, an infant diaper, a sanitary napkin, training pants, a disposable swim suit, an adult incontinent garment, a gasket, etc., the cover 17 is designed to contact the body of the wearer. In these products, the absorbent article 10 can be constructed of a woven or nonwoven material, which is easily penetrated by body fluids. The cover 17 can also be made from natural fibers, synthetic fibers or blends thereof. Suitable materials include bonded-carded webs of polyester, polypropylene, polyethylene, nylon, or other heat-bondable fibers. Other polyolefins, such as copolymers of polypropylene and polyethylene, linear low-density polyethylene, finely perforated film webs and net materials, also work well. A particular preferred material is a composite of an apertured thermoplastic film positioned above a nonwoven fabric material. Such composite material can be formed by extrusion of a polymer onto a web of spunbond material to form an integral sheet. One example of this is an apertured thermoplastic film bonded to a spunbond material. This material exhibits a smooth and soft outer surface, which is not irritating to the wearer's skin and yet has a cushioned feel because of its bulk. In order to allow the cover 17 to expand as the absorbent 12 absorbs fluid, the cover 17 can be elastic or exhibit elastic properties. Alternatively, the cover 17 could be pleated, creped, folded or layered so as to allow expansion and containment of the incoming fluid.

Another preferred material for the cover 17 is a spunbond web of polypropylene. The web can contain from between about 1 percent to about 6 percent of titanium dioxide pigment to give it a clean, white appearance. Other whiteners can also be utilized, such as calcium carbonate. A uniform thickness of spunbond is desirable because it will have sufficient strength, after being perforated in the longitudinal direction, to resist being torn or pulled apart during use. The most preferred polypropylene webs have a weight of between about 18 grams per square meter (gsm) to about 40 gsm. An optimum weight is from between about 30 gsm to about 40 gsm.

Figure 5:
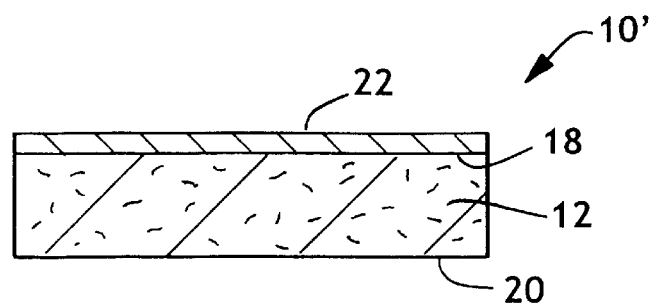
FIG. 5 is a cross-sectional view of an absorbent article having an absorbent and a liquid-permeable cover secured to a surface thereof.

Referring to FIG. 5, an embodiment is depicted showing an absorbent article 10', in the form of an absorbent sheet, which includes an absorbent member 12 having a first major surface 18 and a second major surface 20. Secured to the first major surface 18 is a separate and distinct layer 22. The distinct layer 22 can be a liquid permeable cover or a liquid-impermeable baffle. The materials described above for a liquid permeable cover can be used. The distinct layer 22 can be secured to the absorbent member 12 by means known to those skilled in the art of disposable absorbent products. Common attachment means include the use of a hot or cold melt adhesive, glue, a pressure bond, a heat activated bond, a heat and/or pressure bond, thread, a mechanical fastener such as a thermoplastic staple, etc.

When the layer 22 is a liquid-impermeable baffle, it should permit the passage of air or vapor out of the absorbent article 10' while blocking the passage of body fluids. The liquid-impermeable baffle can be made from any material having these properties. The liquid-impermeable baffle can also be constructed from a material that will block the passage of vapor as well as fluids, if desired. A good material for the liquid-impermeable baffle is a micro-embossed, polymeric film, such as polyethylene or polypropylene. Bicomponent films can also be used. A preferred material is polypropylene film. Most preferably, the liquid-impermeable baffle will be comprised of a polyethylene film having a thickness in the range of from about 0.5 millimeters (mm) to about 2.0 mm.

Figure 6:
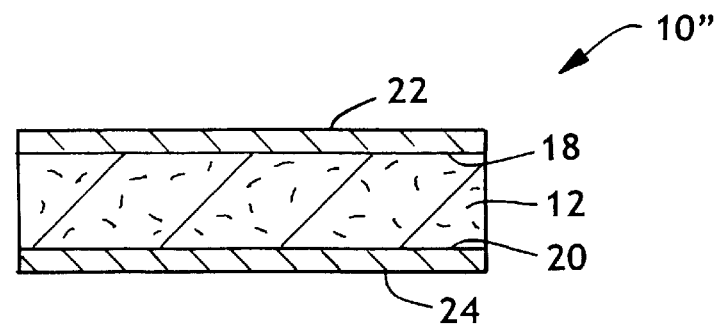
FIG. 6 is a cross-sectional view of an alternative embodiment of an absorbent article having an absorbent with a liquid-permeable cover secured to one surface and a liquid-impermeable baffle secured to an opposite surface.

Referring now to FIG. 6, another embodiment is depicted showing an absorbent article 10", in the form of an absorbent sheet, which includes an absorbent member 12 having a first major surface 18 and a second major surface 20. In this embodiment, a layer 22 is secured to the first major surface 18 of the absorbent member 12 and a layer 24 is secured to the second major surface 20. The layer 22 can be liquid permeable and the layer 24 can be liquid-impermeable. Each layer 22 and 24 can be constructed from the materials identified above.

It should be noted that for certain disposable absorbent products, such as diaper and sanitary napkins, the liquid permeable layer should be aligned adjacent to the body of the wearer. For other types of absorbent products, such as an absorbent pad used in a meat or poultry package to absorb juices, the liquid permeable layer can be aligned away from the food product.

Figure 7:
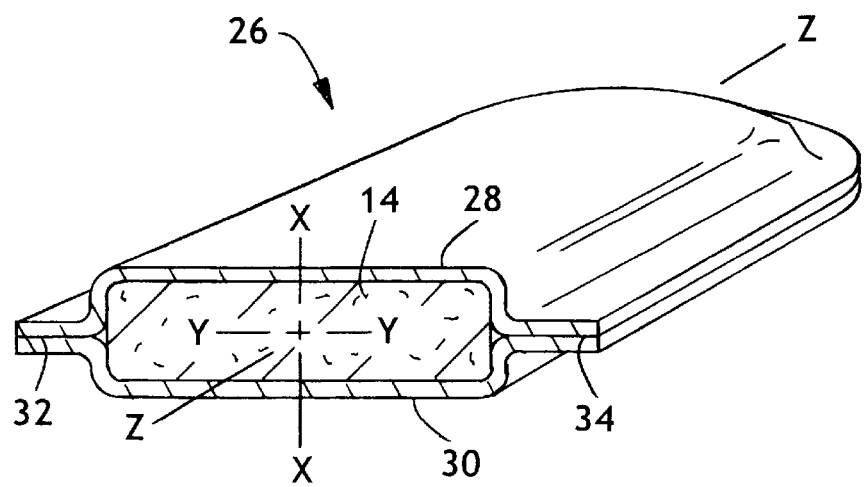
FIG. 7 is a perspective view of an absorbent article having an absorbent enclosed by a liquid-permeable cover and a liquid-impermeable baffle.

Referring to FIG. 7, a disposable product in the form of a sanitary napkin 26 is shown having the absorbent member 14 enclosed by a liquid permeable cover 28 and a liquid-impermeable baffle 30. The absorbent member 14 can be constructed to swell, when wetted, in only one direction, for example, in the x-direction, if desired. Likewise, the absorbent member 14 could be constructed to swell, when wetted, in two directions, or three directions, if that was useful. The cover 28 and the baffle 30 cooperate together to completely enclose the absorbent member 14. This is different from FIG. 6 wherein the layers 22 and 24 only partially enclosed the absorbent member 14. In FIG. 7, the cover 28 and the baffle 30 are joined together to form longitudinal seals 32 and 34 adjacent to the longitudinal sides of the sanitary napkin 26. The ends of the sanitary napkin 26 are also sealed in a similar fashion by joining the cover 28 to the baffle 30.

Figure 8:
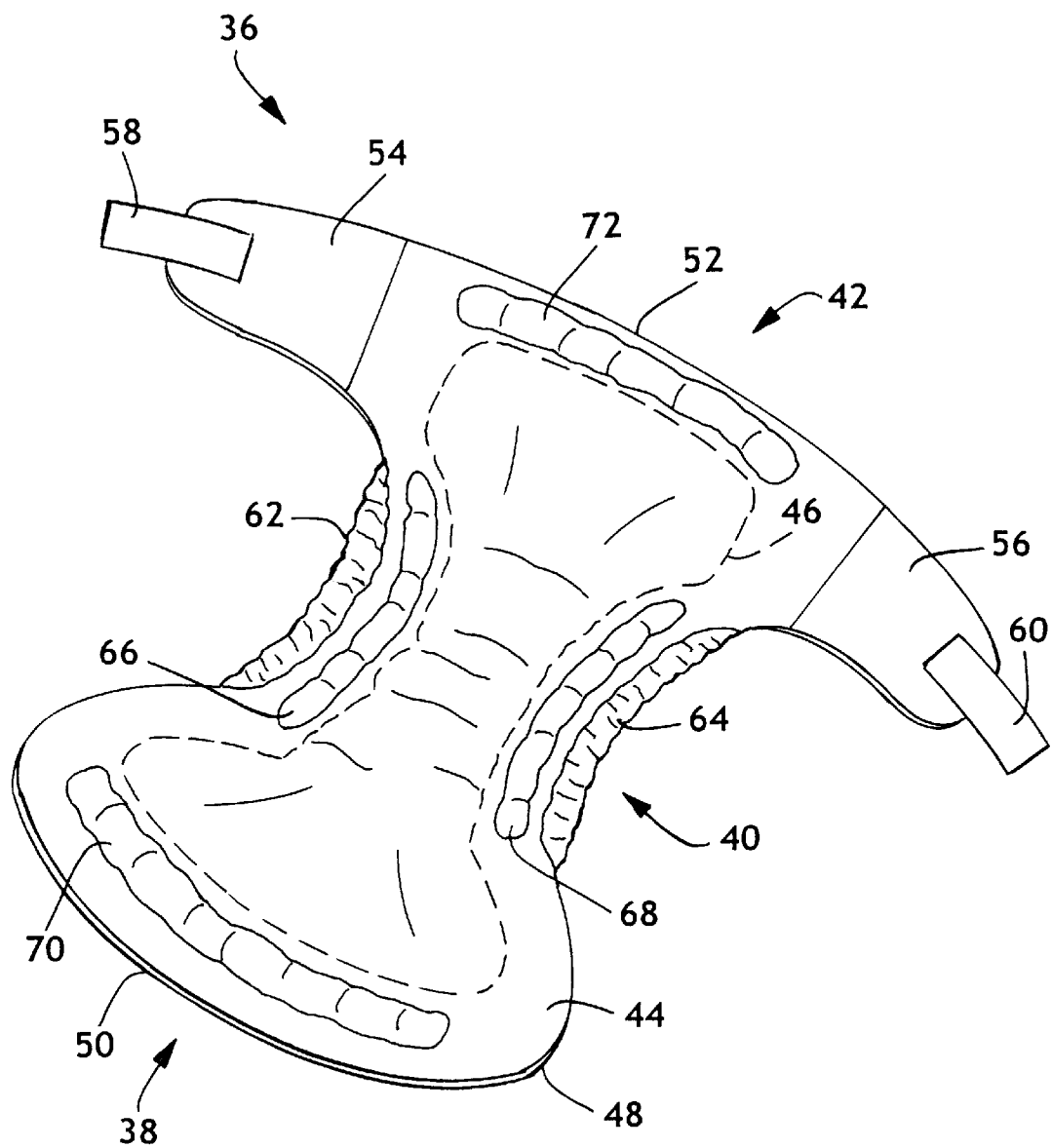
FIG. 8 is a schematic representation of an infant diaper having two strips of absorbent aligned adjacent to the leg cuffs in the crotch section.

Referring to FIG. 8, a disposable infant diaper 36 is shown having a front section 38, a crotch section 40 and a back section 42. The crotch section 40 is located between the front section 38 and the back section 42. The diaper 36 is constructed of a body contacting, liquid permeable cover 44, a main absorbent 46 and a liquid-impermeable baffle 48. The cover 44 and the baffle 48 cooperate to at least partially, and preferably, completely enclose the main absorbent 46. The diaper 36 also has a front edge 50 and a back edge 52. Extending laterally outward from the back edge 52 are ears 54 and 56. Each ear 54 and 56 has an adhesive tab, 58 and 60, respectively. The ears 54 and 56 are designed to wrap around the torso of an infant and the adhesive tabs 58 and 60 are designed to be attached to the front section 38 to hold the diaper 36 securely in place. It should be noted that alternative diaper designs could be utilized which have a second pair of ears extending laterally outward from the front section 38.

The diaper 36 further has a pair of leg cuffs 62 and 64 located on the outer edges of the crotch section 40. Inboard of the leg cuffs 62 and 64 are absorbent gaskets 66 and 68. The absorbent gaskets 66 and 68 can be formed out of the absorbent member 14 disclosed above and can be constructed such that they will expand or swell in one or more directions when wetted by an aqueous fluid, such as urine. In addition, the diaper 36 is depicted with a front, absorbent gasket 70 and a back absorbent gasket 72. The front and back gaskets, 70 and 72 respectively, will prevent fluid leakage out of the diaper 36 adjacent to the waist of the infant. Leakage at these locations can occur when the infant is sleeping or lying on his or her stomach, side or back.

It should be noted that the diaper 36 has a main absorbent member 46 and four separate gaskets 66, 68, 70 and 72. However, a fewer number or a greater number of gaskets could be employed if desired. Likewise, additional absorbent layers could be utilized if desirable. The absorbent that is used to form the main absorbent member 46 and each of the gaskets 66, 68, 70 and 72 can be constructed such that each will optimally perform the function for which it was designed. For example, the main absorbent member 46 can be constructed to expand in the x and y directions as it takes up body fluid while the gaskets 66, 68, 70 and 72 may be designed to swell in the vertical or z-direction as they absorb body fluid. The vertical swelling of the gaskets 66, 68, 70 and 72 will cause a snug seal to form with the body as they expand and this will decrease the likelihood of fluid leaking from the diaper 36 at these locations. Thus one can see that by constructing each absorbent within a particular article a certain way, that the function of the article can be greatly increased. In the case of the diaper 36, the gaskets 66, 68, 70 and 72 will confine the body fluid in the crotch section 40 for a longer period of time and therefor give the main absorbent member 46 added time to absorb the fluid. Additionally, the gaskets 66, 68, 70 and 72 will expand and swell when wetted so as to form dams against the legs and torso of the infant to decrease the likelihood of leakage at these locations. The end result is a much better performing diaper 36 with the use of less absorbent material. Hence, the cost of the diaper may be reduced and the infant may be able to wear the diaper for a longer period of time. Furthermore, by decreasing or preventing the incidences of fluid leakage, there will be fewer times when the outer clothing worn by the infant will be soiled.

Figure 9:
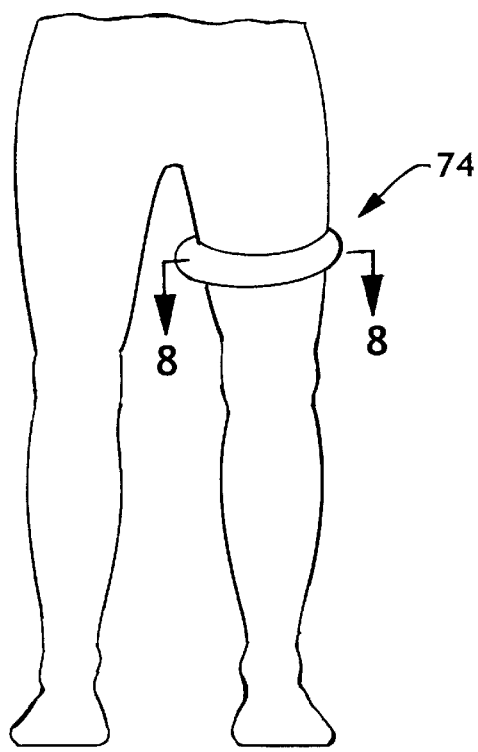
FIG. 9 is a schematic representation of a person with an absorbent article in the form of a gasket applied around his thigh.
Figure 10:
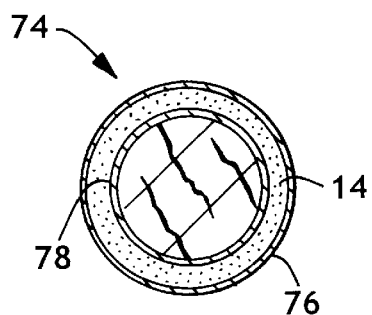
FIG. 10 is a cross-sectional view of the gasket shown in FIG. 7 taken along line 8—8.

Referring to FIGS. 9 and 10, a circular gasket 74 is shown positioned around the thigh of a person for preventing the passage of fluid. The gasket 74 could be sized and configured to be positioned about another limb or appendage of a human body or of an animal. The gasket 74 could be used for medical purposes, i.e. preventing blood from exiting a wound or for absorbent other body fluids, such as urine. The gasket 74 includes an absorbent member 12 at least partially, and preferably completely, enclosed by an outer layer 76 and an inner layer 78. The layers 76 and 78 can be either liquid permeable or liquid-impermeable. The absorbent member 12 should be constructed such that it can expand or swell when wetted in a direction perpendicular to body part it encircles. When the gasket 74 is to prevent the passage of urine down the thigh, the absorbent member 12 will increase in size as urine initially contacts it. As the absorbent swells, a tighter and snugger seal will be formed which will provide greater assurance that additional urine flowing down the thigh will not get past the gasket 74.

One or more of the gaskets 74 could be incorporated into a diaper, training pants, swim suit, etc. and be used to prevent the passage of urine down the thighs of an infant or child. Likewise, two such gaskets 74 could be incorporated into an adult brief and prevent the passage of urine down the thigh of the adult wearer.

Figure 11:
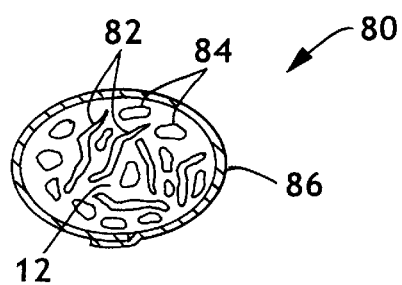
FIG. 11 is a cross-sectional view of an absorbent article constructed of a multitude of fibers and particles enclosed in liquid permeable cover.

Referring to FIG. 11, an alternative embodiment is depicted of an absorbent article 80 having a multitude of fibers 82 and particles 84 enclosed in a liquid permeable cover 86. The absorbent article 80 can be used for a variety of purposes and is especially useful in situations where liquid spills require quick action. For example, in the case where a liquid is spilled onto carpeting, the absorbent article 80 can be rubbed onto the spilled liquid and draw a significant quantity of the liquid out of the absorbent yarns and fibers of the carpeting. The contact and/or pressing of the absorbent article 80 against the wet carpeting will draw the liquid out and retain it in the fibers 82 and in the particles 84. The liquid permeable cover 86 will allow for rapid intake of liquid while retaining the fibers 82 and the particles 84 as a unit for easy disposal. The absorbent article 80 can also be used for taking up a spill on a hard surface. The absorbent article 80 can be constructed to easily absorb up to about 15 grams of liquid per gram of absorbent.

Figure 12:
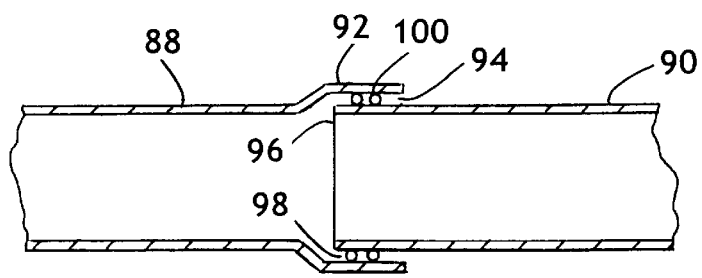
FIG. 12 is an embodiment of an absorbent article in the form of a gasket used to seal two pipe flanges together.

Referring to FIG. 12, first and second pipes, 88 and 90 respectively, are shown. The pipes 88 and 90 can be concrete pipes having a large diameter of about 12 inches or more. The first pipe 88 has an enlarged flange 92 formed on one end 94. The enlarged flange 92 is sized and designed to receive an end 96 of the second pipe 90. When the two pipes 88 and 90 are joined together, a small space 98 will be present. In order to close up the space 98 and form a tight seal between the two pipes 88 and 90, an absorbent gasket 100 can be positioned in the space 98. It has been found that the absorbent gasket 100 can be used where swelling with pressure build-up is desired upon contact with moisture. One particular use is in concrete pipes used to convey sewage and runoff water. When the two pipes 88 and 90 are laid in a trench formed in the ground, a large gap is usually present on either the top or bottom surface of the two pipes 88 and 90. In the past, Oakite® has been used as the gasket material. Oakite® has a rope like appearance and can be pounded into the space between the two pipes to provide a tight seal that would absorb some moisture to prevent leakage. Pounding the Oakite® into position was required because Oakite® has very little wet expansion properties.

The absorbent member 12 of this invention can be formed into the gasket 100 and be placed between the two pipe 88 and 90. The absorbent member 12 exhibits a high pressure for very small expansion conditions and is capable of expanding to a greater extent for larger gaps. Therefore, a loose fitting assembly of two pipes 88 and 90 can easily be sealed by the absorbent gasket 100 when the absorbent member 12 is contacted by a small amount of moisture or water.

It should also be noted that germicides can be added to the absorbent gasket 100 to preclude bacterial degradation when the gasket 100 is in contact with the soil, for example, when used under ground.

The absorbent member 14 can also be formed into other products. One such product is a wiper, which can be used to wipe up spills. Today, most commercially available wipers made from tissue can quickly reach a liquid content that results in leaving a trace, trail or smear of water behind as it reaches its absorbent capacity. A wiper formed from the absorbent 14 of this invention will do away with the likelihood of a trail being left behind because of its ability to absorb additional liquid, as it is wetted.

METHOD

Figure 13:
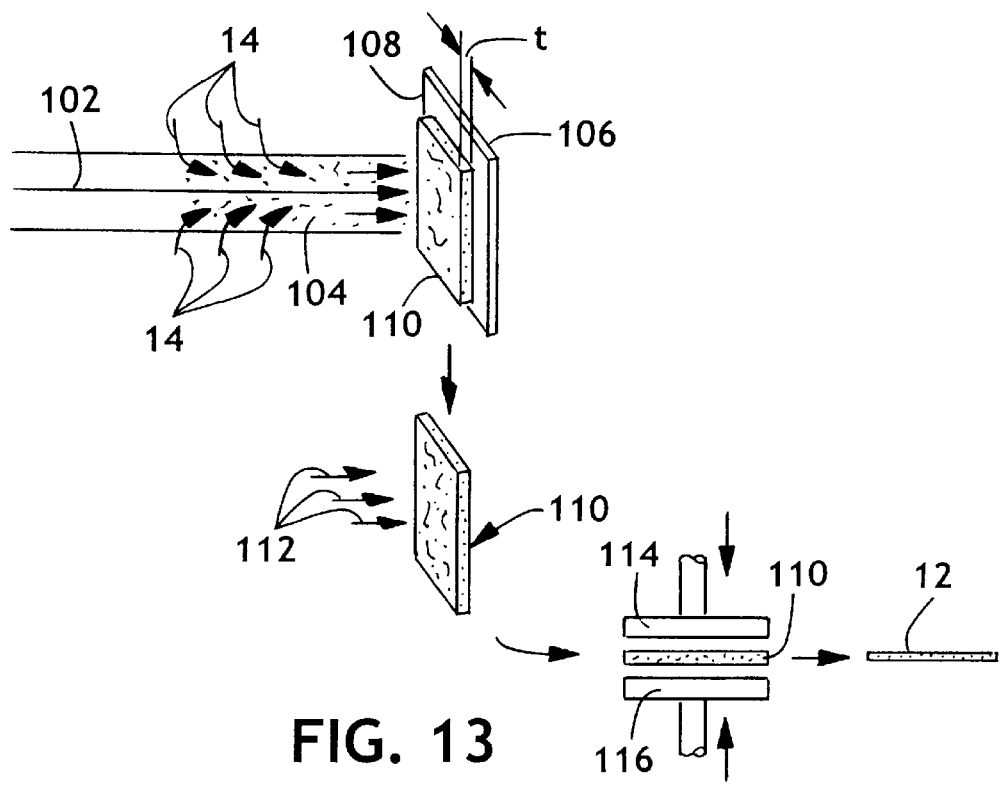
FIG. 13 is a schematic representation of a method for forming an absorbent member.

Referring to FIG. 13, a method is depicted for making an absorbent member 12 from a multitude of the absorbent fibers 14. The method includes introducing multiple fibers 14 of chemi-thermo-mechanical softwood or bleached chemi-thermo-mechanical softwood into an air stream 102. The fibers 14 are entrained in the air stream 102 to form an air-fiber mixture 104. Preferably, the air stream 102 is turbulent to enhance the mixing of the fibers 14.

It should be noted that the method described above refers to introducing the fibers 14 into the air stream 102. However, particles 84, as described in reference to FIG. 11, could also be introduced in conjunction with the fibers 14, if desired.

The air-fiber mixture 104 is then directed to a porous media 106, such as a wire mesh screen. The porous media 106 has a first surface 108 that receives the initial contact by the air-fiber stream. The size and configuration of the porous media 106 can vary. For good results, a wire mesh value of "32 Standard Mesh" works well. Alternatively, the porous media 106 can be a perforated plate having a plurality of circular apertures formed therethrough. A perforated plate having a plurality of apertures of about 0.038 inches in diameter with a 0.050 spacing therebetween work well. The above referenced plate will have an open area of about 45%. It should be noted that the dimensions of the apertures and the land areas could vary to suit one's particular needs.

It should be further noted that the porous media 106 could be a tissue sheet, a nonwoven sheet, a porous wire, a screen or some other structure. The porous media 106 could be planar in configuration or have an arcuate surface in one or more directions. When the porous media 106 has one or more arcuate surfaces, it allows forming the absorbent member 12 on drums as well as the forming of three-dimensional shapes.

The air-fiber mixture 104 should be uniformly distributed over the entire first surface 108 of the porous media 106 with a pressure differential across the porous media 106 ranging from between about 3 to about 30 inches of water pressure. The air portion of the mixture 104 will pass through the porous media 106 while the fibers 14 will collect on the first surface 108. As the air passes through the porous media 106, it will leave the fibers 14 behind. The air can then be recycled and reused, if desired. The multitude of fibers 14 are separated from the air and build up into a mat on the first surface 108 of the porous media 106. The porous media 106 acts like a filter separating the fibers 14 from the air stream 102. When the desired amount of fibers 14 have accumulated into a fibrous mat 110 having a predetermined thickness "t", the air stream 102 is stopped or halted. The air stream 102 can either be diverted away or be turned off as in an intermittent operation. The amount of fibers 14 accumulated to form the fibrous mat 110 can vary from between about 20 to about 1,000 grams of fibers per square meter.

The fibrous mat 110 is then removed from the first surface 108 of the porous media 106. The fibrous mat 110 can be weighted to determine its basis weight and moisture content. Water 112 is then added to the fibrous mat 110 to obtain a predetermined percent of moisture. This predetermined moisture value can be any desired value, for example, 5%, 10%, 15%, etc. depending on the later steps of the process. The water 112 can be added to the fibrous mat 110 in a number of different ways. Some of these ways include: misting the water 112 over the fibrous mat 110, placing the fibrous mat 110 in a humidity chamber, or passing steam through the fibrous mat 110. The amount of water 112 added would determine the weight gain of the fibrous mat 110. Knowing the initial basis weight of the fibrous mat 110 and the basis weight of the fibrous mat 110 after the addition of a certain amount of water 112, one can control the percent moisture in the fibrous mat 110. The initial amount of water 112 present in the fibers 14 making up the fibrous mat 110 will partially determine how much water 112 should be added. The amount of water 112 added is established by knowing the water level of the fibers 14 before adding additional water 112. This can be determined by weighing a sample of the fibers 14 and then placing the fibers 14 in a balance which is in a heated environment (greater than about 100° C.) to evaporate any moisture until there is no further weight loss. The weight difference divided by the original weight is the portion of water present. Therefore, the amount of water 112 needed to be added to the fibrous mat 110 can be established from the desired moisture percentage (for example, 10%), and the measured initial moisture level.

Immediately following the addition of the water 112, the fibrous mat 110 is subjected to a stressing condition and/or a compression step. The compression of the fibrous mat 110 can be accomplished by using a pair of flat platens to create a one dimensional change or by using configured platens to create a curved or arcuately stressed absorbent structure. The amount the fibrous mat 110 is compressed can be limited by the desire final thickness "t" of the absorbent member 12 or be limited by the desired maximum pressure that can be applied during the compression step.

Referring again to FIG. 13, the fibrous mat 110 is placed between two platens 114 and 116, at least one of which is movable. The platens 114 and 116 can be heated, if desired, to drive off excess moisture when present. As the first platen 114 moves toward the second platen 116, the absorbent sheet 12 is compressed to a desired thickness. Besides using a pair of platens 114 and 116, the absorbent sheet 12 can be compressed by using a standard press or by conveying the absorbent sheet 12 through the nip of a pair of close or contacting pressure rolls.

It has been found that if a final nip compression of about 0.03 inches is desired for a fibrous mat 110 having an initial thickness of about 2 inches, that the compression should be done in a progressive series of steps. The steps will depend upon the diameter of the pressure rolls. One sequence would be to compress the fibrous mat 110 from an initial thickness of about 2 inches (about 51 mm) down to about 0.25 inches (about 6.4 mm). The next step is to compress the fibrous mat 110 down from about 0.25 inches (about 6.4 mm) to about 0.03 inches (about 0.76 mm). This can be accomplished using a 12 inch (305 mm) diameter steel roll interacting with a 4 inch (102 mm) diameter steel roll. This is the final step in the making of the absorbent member 12. Depending upon the moisture level, it is sometimes desirable to compress the fibrous mat 110 to less than the desired thickness and allow the absorbent member 12 to spring back to the desired thickness. For example, compress the fibrous mat 110 to a thickness of about 0.027 inches (about 0.69 mm) and allow it to spring back to a thickness of about 0.03 inches (about 0.76 mm).

Figure 14:
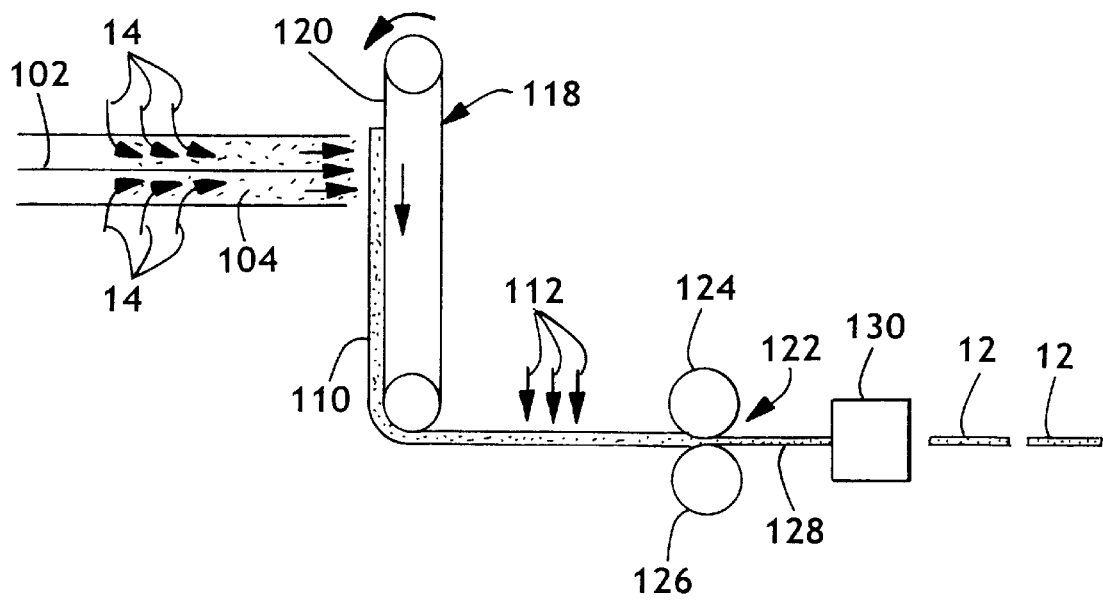
FIG. 14 is a schematic representation of a continuous method for forming an absorbent member.

Referring to FIG. 14, a method is depicted for forming an absorbent member 12 in a continuous fashion. This method includes introducing the fibers 14 into the air stream 102 and forming an air-fiber mixture 104. This air-fiber mixture 104 is then directed to an endless belt 118. The endless belt 118 can be formed as a fine mesh wire and has an outer surface 120. The fibers 14 will collect on the outer surface 120 of the belt 118 while the air portion of the mixture 104 will be allowed to pass through the endless belt and be recovered, if desired. The level of pressure differential maintained across the endless belt 118 will affect the density of the fibrous mat 110. At about 3 inches (about 76 mm) of water pressure, the bulk density of the fibrous mat 110 could be 0.01 grams/cubic centimeter (g/cc), while at about 30 inches (about 762 mm) of water pressure, the density could reach 0.1 g/cc. The linear speed of the endless belt 118 will affect the length of the forming chamber needed to deposit adequate fiber 14 for forming the fibrous mat 110.

The fibrous mat 110 formed on the endless belt 118 is then stripped off of the outer surface 120 and is contacted with water 112. The water 112 can be sprayed or misted onto one or both sides of the fibrous mat 110. Preferably, a preselected amount of water 112 is sprayed over the entire width of the fibrous mat 110. This provides for a uniform distribution of hydrogen bonding to occur throughout the entire fibrous mat 110. The fibrous mat 110 is then routed through a nip 122 formed by two interacting pressure rolls 124 and 126. The pressure rolls 124 and 126 can be heated to remove any excess moisture from the fibrous mat 110, if required. The compression nip 122 will densify the fiber network and allow hydrogen bonding to occur and form a compressed fibrous mat 128. The compressed fibrous mat 128 can then be routed to a slitter and cutter 130 where the compressed fibrous mat 128 is cut and/or slit into desired sizes of absorbent member 12. Alternatively, the compressed fibrous mat 128 can be directed away from the slitter 130 and be rolled up onto hollow cores to form finished rolls, if desired.

Figure 15:
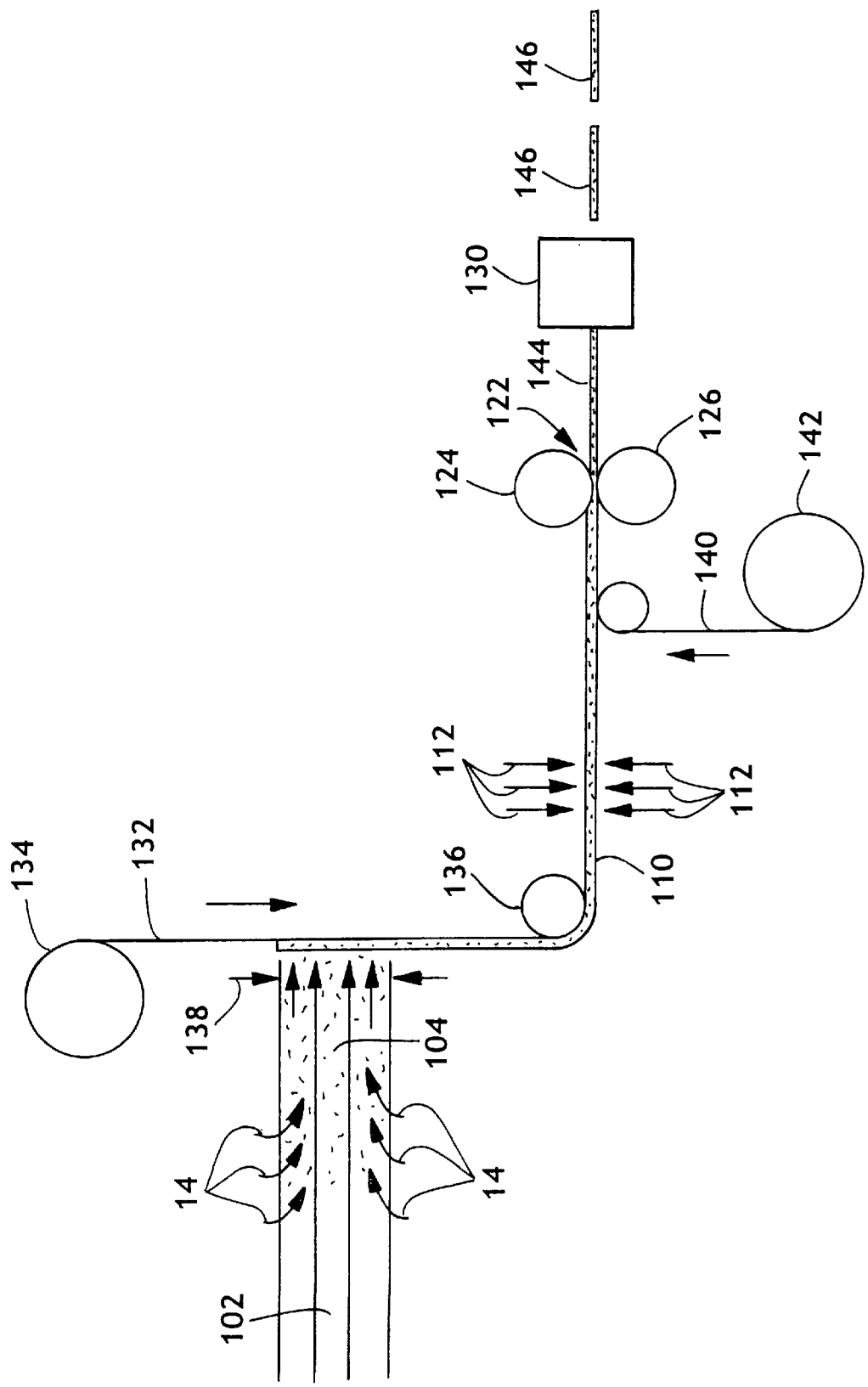
FIG. 15 is a schematic representation of an alternative method for continuous forming an absorbent member.

Referring now to FIG. 15, still another alternative method is depicted for continuously forming an absorbent member 12. This method includes introducing the fibers 14 into the air stream 102 and forming an air-fiber mixture 104. This air-fiber mixture 104 is then directed onto a continuous first layer 132. The first layer 132 is unwound from a supply roll 134 and is conveyed by a drive mechanism 136 in a desired direction. The first layer 132 can be a porous tissue, a nonwoven fabric or any other type of natural or synthetic material. The drive mechanism 136 can be a drive motor, an endless belt, or some other type of means to pull or draw the first layer 132 along. As the first layer 132 is unwound from the supply roll 134 it is conveyed pass a location 138 where the air-fiber mixture 104 is deposited thereon.

The air-fiber mixture 104 can be deposited onto the first layer 132 at a single location 138 or it can be deposited onto the first layer 132 at multiple locations (not shown), to progressively build up the fibers 14. The thickness of the fibrous mat 110 can be varied by controlling the rate at which the air-fiber mixture 104 is deposited onto the first layer 132 and by controlling the speed of the first layer 132.

As taught above for FIG. 14, water 112 can be directed onto one or both sides of the fibrous mat 110. After the addition of the water 112, a second layer 140 can be added to the fibrous mat 110. The second layer 140 can be unwound from a supply roll 142 and can be similar or different from the first layer sheet 132. It should be noted that either one or both of the first and second layers, 132 and 140 respectively, can become part of the finished absorbent 12. For example, the first layer 132 can be a liquid permeable cover and the second layer 140 can be a liquid-impermeable baffle. The finished product would be a laminate of all three layers, cover 132, fibrous mat 110 and baffle 140.

When the first and/or second layers 132 and/or 140 respectively, are constructed from porous materials such as tissue, nonwovens or textiles, the fibrous mat 110 will have a tendency to mechanically attach to the adjacent layer(s) when the composite is routed through the compression nip 122. Impervious layers, such as polymer films, can be attached to the fibrous mat 110 with an adhesive or by a corona treatment before passing the layers through the compression nip 122.

If it is desirable to increase fiber integrity of the fibrous mat 110, this can be accomplished by adding binder fibers. The binder fibers can be mixed with the fibers 14 within the air stream 102 to form the mixture 104 which is then deposited onto the first layer 132. To increase integrity, long fibers having a length of greater than about 4 mm can be added to the air stream 102. The long fibers will provide mechanical entanglement and friction. Materials such as rayon, cotton, wool, etc. are good for introducing long fibers into the fibrous mat 110.

Furthermore, thermal-setting fibers can be mixed into the air stream 102 to increase integrity. One type of thermal-setting fibers is known as "Pulpex" and is available from Hercules Inc. Hercules Inc. has a sales office in Wilmington, Del. Thermal-setting fibers can also be blown directly into the air stream, e.g., melt blown fibers. These thermal-setting fibers should be heated and cooled while the fibrous mat 110 has its lowest density and before compression and hydrogen bonding. The use of a heated compression nip 122 can be adverse if it allows for thermal bonding between the fibers in the compressed high-density state. Therefore, a heated compression nip should be avoided when thermal-setting fibers are utilized.

Once the first and second layers, 132 and 140 respectively and the fibrous mat 110 pass through the nip rollers 124 and 126, a compressed fibrous mat 144 if formed. This compressed fibrous mat 144 can be directed to a slitter 130, as explained above, to form individual articles 146. Alternatively, the compressed fibrous mat 144 can be rolled up into a larger roll, if desired.

Other chemical or particles can also be included within the fibrous mat 110 by introducing them into the air stream 102 with the fibers 14. Such chemicals and particles could include superabsorbent particles or materials, deodorant particles, encapsulated dyes, encapsulated fragrances, catalyst particles, germicidal particles, etc.

It is also possible to stress the fibers 14 within the fibrous mat 110. By using the method described above, one can introduce the fibers 14 into the air stream 102 to form entrained fibers in the turbulent air-fiber mixture 104. These fibers 14 are then separated out of the air-fiber mixture at the porous medial 106, the endless belt 118 or at the carrier sheet 132. When the fibers 14 are deposited using gravity onto a surface or by using electrostatic attraction of the fibers 14 onto a surface, a low-density (less than about 0.1 gram/cc) fibrous mat 110 is created. This low density fibrous mat 110 has the fibers 14 arranged in a random orientation, for example, the long axis of the fibers 14 are likely to be oriented in the x, y and z directions. When the fibers 14 contain a significant percentage of their original lignin content, for example about 80%, there will be stresses developed within the fibers 14 when they are bent, twisted, contorted, crushed, or otherwise changed from their relaxed shape. By using an external constraint and force, a large number of the fibers 14 can become contorted and hence stressed into a dense condition. This enables one to change the fibers 14 from a condition of low density to a condition of high density. Due to the random orientation of the fibers 14, a large percentage of the fibers 14 will have significant movement while being compressed. For example, the thickness of the fibrous mat 110 can be reduced from about 2 inches (about 51 mm) to a thickness of about 0.03 inches (about 0.76 mm). This movement during compression, along with the potential for many of the different fibers 14 to impede or limit any one fiber from moving relative to its full length, leads to a stressed condition.

Stressing of the fibers 14 in two or three directions can be induced by successive partial compression of the fibers 14 in two or three different directions. Compression in three different directions can be achieved by forcing the low density fibers 14 through a funnel shaped extruder where the progressively smaller diameters will compress the fibers 14 in a radial direction while the pushing mechanism will compress the fibers 14 in an axial direction. The addition of moisture to the fibers 14 will facilitate hydrogen bonding in the compressed condition. The stresses created in the fibers 14 and in the fibrous mat 110 will show directionality when the stresses are relieved. This means that when the hydrogen bonds are broken, the fibers 14 will want to expand outward in a direction opposite to the direction in which they were compressed. An example of this was carried out in a test laboratory. Bleached chemi-thermo-mechanical softwood fibers 14 where collected and formed into a fibrous mat 110 using the method depicted in FIG. 13. The fibrous mat 110 had an initial density of 0.02 gram/cc and a thickness of about 2 inches (about 51 mm). The moisture level in the fibrous mat 110 was adjusted up to about 10% and the fibrous mat 110 was compressed in one direction (the z direction) to reduce its thickness down to about 0.03 inches (about 0.76 mm). Water was then applied to the fibrous mat 110 to cause expansion and swelling. The expansion was almost entirely in the z-direction, opposite to the force vector that was used to compress the fibrous mat 110. The saturated fibrous mat 110 expanded from a thickness of about 0.03 inches (about 0.76 mm) to a thickness of about 0.25 inches (about 0.64 mm) or an increase of about 700%. There was only minimal expansion in the x and y directions of about 10% to about 20%.

While the invention has been described in conjunction with a specific embodiment, it is to be understood that many alternatives, modifications and variations will be apparent to those skilled in the art in light of the aforegoing description. Accordingly, this invention is intended to embrace all such alternatives, modifications and variations that fall within the spirit and scope of the appended claims.

We claim:

1. An absorbent article comprising an absorbent member formed of a multitude of randomly oriented chemi-thermo-mechanical cellulosic fibers containing at least about 20% lignin within said cellulosic fibers, said absorbent member having a moisture content of from between about 1% to about 20% water by weight of fiber, said fibers being elastically stressed and bonded by hydrogen bonds and being retained in a stressed condition, said hydrogen bonds being breakable upon contact with an aqueous fluid thereby allowing rapid expansion of said absorbent member, and said absorbent member having a density of from between about 0.2 g/cc to about 1 g/cc.

2. The absorbent article of claim 1 wherein said absorbent member is an absorbent sheet which has a first major surface and said first major surface is secured to a liquid permeable cover.

3. The absorbent article of claim 2 wherein said absorbent sheet has a second major surface and said second major surface is secured to a liquid-impermeable baffle.

4. The absorbent article of claim 1 wherein said absorbent member is an absorbent sheet which has a first major surface and said first major surface is secured to a liquid-impermeable baffle.

5. An absorbent article comprising:
   a) an absorbent member including a multitude of randomly oriented chemi-thermo-mechanical cellulosic fibers containing at least about 20% lignin within said cellulosic fibers, said absorbent member having a moisture content of from between about 1% to about 20% water by weight of fiber, said fibers being elastically stressed and bonded by hydrogen bonds and being retained in a stressed condition, said hydrogen bonds being breakable upon contact with an aqueous fluid thereby allowing rapid expansion of said absorbent member, and said absorbent member having a density of from between about 0.2 g/cc to about 1 g/cc and having the capacity to absorb from between about 1 gram of fluid per gram of absorbent to about 18 grams of fluid per gram of absorbent; and
   b) a cover which at least partially surrounds said absorbent member.

6. The absorbent article of claim 5 wherein said absorbent member has the capacity to absorb from between about 1 to about 15 grams of fluid per gram of absorbent.

7. The absorbent article of claim 5 wherein said absorbent member has an initial volume and said absorbent is capable of expanding from between about 5 to about 8 times said initial volume as said absorbent member absorbs an aqueous fluid.

8. The absorbent article of claim 5 wherein said chemi-thermo-mechanical cellulosic fibers are softwood fibers.

9. The absorbent article of claim 8 wherein said chemi-thermo-mechanical softwood fibers are bleached.

10. An absorbent article comprising:
   a) an absorbent member including a plurality of randomly oriented chemi-thermo-mechanical cellulosic fibers and cellulosic particles, each fiber containing at least about 20% lignin within said cellulosic fibers, said absorbent member having a moisture content of from between about 1% to about 20% water by weight of a combination of fiber and particle, said fibers being elastically stressed and bonded by hydrogen bonds and being retained in a stressed condition, said hydrogen bonds being breakable upon contact with an aqueous fluid thereby allowing rapid expansion of said absorbent member, and said said absorbent member having a density of from between about 0.5 g/cc to about 1 g/cc; and
   b) an expandable cover completely enclosing said absorbent member.

11. The absorbent article of claim 10 wherein said absorbent member has a capacity to absorb from between about 1 to about 18 grams of fluid per gram of absorbent.

12. The absorbent article of claim 10 wherein said chemi-thermo-mechanical cellulosic fibers are bleached.

13. The absorbent article of claim 10 wherein said chemi-thermo-mechanical fibers are softwood fibers.

14. The absorbent article of claim 10 wherein said article is a bed pad.

15. An absorbent article comprising:
   a) an absorbent member including a multitude of randomly oriented chemi-thermo-mechanical cellulosic fibers containing at least about 20% lignin within said cellulosic fibers, said absorbent member having a moisture content of from between about 1% to about 20% water by weight of fiber, said fibers being elastically stressed and bonded by hydrogen bonds and being retained in a stressed condition, said hydrogen bonds being breakable upon contact with an aqueous fluid thereby allowing rapid expansion of said absorbent member, and said absorbent member having a density of from between about 0.5 g/cc to about 1 g/cc and having a first major surface and a second major surface;
   b) a liquid permeable bodyside cover positioned adjacent to said first major surface; and
   c) a liquid-impermeable baffle positioned adjacent to said second major surface.

16. The absorbent article of claim 15 wherein said cover and baffle cooperate together to enclose said absorbent member and expand as said absorbent member increases in size.

17. The absorbent article of claim 15 wherein said absorbent member has a capacity to absorb from between about 1 to about 18 grams of fluid per gram of absorbent.

18. The absorbent article of claim 15 wherein said absorbent article is a disposable diaper.

19. An absorbent article comprising:
a) an absorbent member enclosed by said cover, said absorbent member including a multitude of randomly oriented chemi-thermo-mechanical cellulosic fibers containing at least about 20% lignin within said cellulosic fibers, said absorbent having a moisture content of from between about 1% to about 20% water by weight of fiber, said fibers being elastically stressed and bonded by hydrogen bonds and being retained in a stressed condition, said hydrogen bonds being breakable upon contact with an aqueous fluid thereby allowing rapid expansion of said absorbent member, and said absorbent member having a density of from between about 0.5 g/cc to about 1 g/cc and capable of absorbing at least about 10 grams of fluid per gram of absorbent;
b) a liquid permeable bodyside cover;
c) a liquid-impermeable bodyside baffle, said cover and baffle cooperating together to enclose said absorbent member.

20. The absorbent article of claim 15 wherein said absorbent article is a gasket.

21. The absorbent article of claim 15 wherein said absorbent article is a wiper.

* * * * *